(12) United States Patent
Chai et al.

(10) Patent No.: US 11,893,472 B2
(45) Date of Patent: Feb. 6, 2024

(54) ACCURACY COMPENSATION METHOD FOR DISCHARGE CAUSTIC ALKALI CONCENTRATION MEASURING DEVICE IN EVAPORATION PROCESS

(71) Applicant: NORTHEASTERN UNIVERSITY, Liaoning (CN)

(72) Inventors: Tianyou Chai, Liaoning (CN); Yao Jia, Liaoning (CN); Liangyong Wang, Liaoning (CN)

(73) Assignee: Northeastern University, Liaoning (CN)

( * ) Notice: Subject to any disclaimer, the term of this patent is extended or adjusted under 35 U.S.C. 154(b) by 64 days.

(21) Appl. No.: 17/309,942

(22) PCT Filed: Jul. 21, 2020

(86) PCT No.: PCT/CN2020/103203
§ 371 (c)(1),
(2) Date: Jul. 1, 2021

(87) PCT Pub. No.: WO2021/093362
PCT Pub. Date: May 20, 2021

(65) Prior Publication Data
US 2022/0083839 A1    Mar. 17, 2022

(30) Foreign Application Priority Data
Nov. 11, 2019 (CN) .......................... 201911096987.0

(51) Int. Cl.
*G06N 3/044* (2023.01)
*G01N 33/00* (2006.01)
*G06F 17/17* (2006.01)
(52) U.S. Cl.
CPC ............. *G06N 3/044* (2023.01); *G01N 33/00* (2013.01); *G06F 17/17* (2013.01)

(58) Field of Classification Search
CPC ........ G01N 33/00; G06N 3/044; G06N 3/045; G06N 3/084; G06F 17/17; C01F 7/06; C01F 7/14
See application file for complete search history.

(56) References Cited

U.S. PATENT DOCUMENTS 9,212,989 B2 * 12/2015 Little ................. G01N 21/3504
2014/0054464 A1    2/2014 Lake et al.

FOREIGN PATENT DOCUMENTS

| CN | 101281182 A | 10/2008 |
| CN | 102809966 A | 12/2012 |

(Continued)

OTHER PUBLICATIONS

English translation of CN 101281182 A, Wang et al, Soft measuring method of sodium aluminate solution component concentration, 2008, 5 pages. (Year: 2008).*

(Continued)

*Primary Examiner* — Tung S Lau
*Assistant Examiner* — Dacthang P Ngo
(74) *Attorney, Agent, or Firm* — NKL Law; Allen Xue

(57) ABSTRACT

Disclosed is an accuracy compensation method for discharge caustic alkali concentration measuring device in evaporation process, comprising following steps: step 1. collecting process data of instrument values and laboratory values of alkali liquor refractive index, temperature and caustic alkali concentration in the evaporation process; step 2. performing sliding average filtering, time series matching and normalization on the process data collected in step 1 to obtain preprocessed process data; step 3. inputting the preprocessed process data into an accuracy compensation model of the caustic alkali concentration measuring device to obtain compensation values; step 4. adding the compensation values of the caustic alkali concentration to the instrument values to realize on-line compensation of the (Continued)

caustic alkali concentration. The disclosed can accurately compensate the concentration value measured by the on-line instrument, and the compensated concentration value can follow the actual change trend; moreover, the measurement accuracy can meet the needs of actual production.

5 Claims, 6 Drawing Sheets

(56) References Cited

FOREIGN PATENT DOCUMENTS

| CN | 105821170 A | 8/2016 |
|---|---|---|
| CN | 107168255 A | 9/2017 |
| CN | 108304823 A | 7/2018 |
| CN | 109740742 A | 5/2019 |
| CN | 110096755 A | 8/2019 |
| CN | 110208453 A | 9/2019 |
| CN | 110794093 A | 2/2020 |

OTHER PUBLICATIONS

Wang, Wei et al.; Modeling Component Concentrations of Sodium Aluminate Solution via Hammerstein Recurrent Neural Networks; IEEE Transaction on control systems technology, vol. 20, No. 4, Jul. 4, 2012, pp. 971-982.

Wang, Wei et al.; Soft Sensing of Sodium Aluminate Solution Component Concentrations via on-line Clustering and Fuzzy Modeling; American Control Conference; Jun. 29-Jul. 1, 2011, pp. 2468-2473.

Ren, Xiaoye et al.; Shadow Effect Compensation of Ultrasonic Wind Measure Based on Fluent and LSTM Neural Network; Computer Applications and Software, vol. 36, No. 7, Jul. 2019, pp. 89-98.

Wang, Wei et al.; Sodium Carbonate Fuzzy Modeling using Stabel Learning; J Tsinghua Univ (Sci & Tech), 2012, vol. 52, No. 9, ISSn 1000-0054, pp. 1210-1217.

Wang, Wei et al.; Research of Ellipsoid Bounded Algorithm in Hybrid Modeling; Acta Sutomatica Sinica; vol. 40, No. 9, Sep. 2014, pp. 1875-1881.

Wang, Yonggang et al.; Hybrid Intelligent Optimal Control for Alumina Evaporation Processes; CIESC Journal vol. 64, No. 12, Dec. 2013, pp. 4342-4347.

Sun, Zhanhai et al.; Study on Soft-sensing Method of Component Concentration of Sodium Aluminate Solution in Alumina Production Process; China Science and Technology Journal Database; 1671-5802(2015)12-0241-02, 2015 vol. 12, pp. 241-242.

* cited by examiner

ACCURACY COMPENSATION METHOD FOR DISCHARGE CAUSTIC ALKALI CONCENTRATION MEASURING DEVICE IN EVAPORATION PROCESS

FIELD OF THE INVENTION

The invention relates to the technical field of compensation of measuring devices for production parameters in the evaporation process of alumina, in particular to an accuracy compensation method for a discharge caustic alkali concentration measuring device in an evaporation process.

BACKGROUND

The caustic alkali concentration is a key process index in the evaporation process of alumina. Whether the caustic alkali concentration is qualified or not will directly affect the ratio of grinding process and the dissolution rate of dissolution process of alumina, thus affecting the quality of final product of alumina. Therefore, on-line measuring of the caustic alkali concentration is a very important task in alumina production.

At present, there are usually two methods to detect the concentration of the caustic alkali. One method is to obtain it by manual sampling and laboratory test after the preparation of alkali liquor in the evaporation process. Because the sampling interval is long (usually 2 hours or 4 hours) and the laboratory test takes a long time, there is a serious lag in the measuring of the caustic alkali concentration. It is easy to cause large fluctuations in the concentration of the caustic alkali and a low qualification rate of alkali liquor by using these seriously lagging information to guide the production, resulting in difficulties in controlling other processes, and ultimately resulting in low alumina quality. The other method is using caustic alkali concentration on-line measuring instruments, but these on-line instruments are expensive, and usually the internal model parameters of the instruments are fixed after installation. Since the raw ore composition used by some alumina enterprises fluctuates greatly, the evaporation process conditions are complex and changeable. Therefore, with the passage of time, the output value of the on-line measuring device may drift, the accuracy of the instruments may decrease, and the enterprises need to invest a lot of money in maintenance, and the recalibration process is cumbersome.

SUMMARY OF THE INVENTION

1. Technical Problems to be Solved

Aiming at solving the existing technical problems, the present invention provides an accuracy compensation method for a discharge caustic alkali concentration measuring device in an evaporation process.

2. Technical Solutions

In order to achieve the above objectives, the main technical solution provided by the present invention includes:

An accuracy compensation method for a discharge caustic alkali concentration measuring device in an evaporation process comprises that following steps:
 step 1. data acquisition: collecting process data of alkali liquor refractive index, temperature and instrument values and laboratory values of caustic alkali concentration in the evaporation process;
 step 2. data preprocessing: performing sliding average filtering, time series matching and normalization on the process data collected in step 1 to obtain preprocessed process data;
 step 3. inputting the preprocessed process data into an accuracy compensation model of the caustic alkali concentration measuring device to obtain compensation values;
 step 4. adding the compensation values of the caustic alkali concentration to the instrument values to realize the on-line compensation of the caustic alkali concentration.

Preferably, during the sliding average filtering process in step 2, a window length of the sliding average filtering is set, that is, the number of points of the sliding average filtering is N, and the filtering formula is:

$$X(t) = \frac{1}{N}\sum_{i=0}^{N-1} X'(t-i) \quad (1)$$

wherein, $X(t)$ is a value at time t after filtering, $X'(t)$ is a value of an original data at time t, and N is the window length of the sliding average filtering.

Preferably, during the time series matching process in step 2, the process data of 2 hours is divided into 3 parts according to an optimized control period of 40 minutes, and each part takes an average value of the process data of 40 minutes, the average value corresponds to the laboratory data of the previous sampling;
 wherein a formula for the time series matching is:

$$\begin{cases} X(k) = \frac{1}{40}\sum_{i=0}^{39} X(i) \\ X(k+1) = \frac{1}{40}\sum_{i=40}^{79} X(i) \\ X(k+2) = \frac{1}{40}\sum_{i=80}^{119} X(i) \end{cases} \quad (2)$$

where $X(i)$ is a value at the $i^{th}$ time after filtering, and $X(k)$ is process data matching a laboratory value at the $k^{th}$ point.

Preferably, the normalization in step 2 normalizes states of input and output variables used in the accuracy compensation model of the caustic alkali concentration measuring device:

$$\hat{x}_n = \frac{x_n - x_{min}}{x_{max} - x_{min}} \quad (3)$$

wherein, for a historical data $X=[x_1, \ldots, x_n]$ of a certain variable data, $x_n$ represents a state of the variable at the $n^{th}$ point, $x_{max}$ represents the maximum value of the variable in all the historical data, and $x_{min}$ represents the minimum value of the variable in all the historical data.

The input variables are preprocessed process data, and the output variables are the compensation values.

Preferably, the method also includes constructing an accuracy compensation model of the caustic alkali concentration measuring device, and training model parameters.

Preferably, constructing the accuracy compensation model of the caustic alkali concentration measuring device comprises the following steps:

Taking selected historical process data and errors between historical instrument values of the caustic alkali concentration and historical laboratory values as input and output training data of the accuracy compensation model of the caustic alkali concentration measuring device, and using a deep learning algorithm to construct the accuracy compensation model;

Using a double-layer LSTM (Long Short-Term Memory) network for the deep learning algorithm to establish the accuracy compensation model of the caustic alkali concentration measuring device.

Preferably, the compensation method further comprises evaluating the accuracy compensation model of the caustic alkali concentration measuring device by using a root mean square error, a mean absolute error, and a mean absolute percentage error:

wherein a formula for calculating the root mean square error is:

$$RMSE = \sqrt{\frac{\sum_{i=0}^{N-1}(y_i - \hat{y}_i)^2}{N}} \quad (4)$$

wherein a formula for calculating the mean absolute error is:

$$MAE = \frac{\sum_{i=0}^{N-1}|y_i - \hat{y}_i|}{N} \quad (5)$$

wherein a formula for calculating the mean absolute percentage error is:

$$MAPE = \frac{100}{N}\sum_{i=0}^{N-1}\left|\frac{y_i - \hat{y}_i}{y_i}\right| \quad (6)$$

wherein, $y_i$ is laboratory values of the $i^{th}$ group of samples, and $\hat{y}_i$ is compensated caustic alkali concentration values of the $i^{th}$ group of samples.

3. Beneficial Effects

According to the accuracy compensation method for a discharge caustic alkali concentration measuring device in an evaporation process provided by the present invention, a large dataset is formed by collecting input and output data and laboratory data of an internal model of the caustic alkali concentration on-line measuring device, then a deep learning algorithm is adopted to construct and train the accuracy compensation model of the caustic alkali concentration measuring device so as to form a complete caustic alkali concentration model, and real-time data of the production process is used to realize on-line compensation of the caustic alkali concentration. On this basis, the optimization of feed rate, steam pressure and the amount of newly added alkali in the evaporation process can be guided, and the caustic alkali concentration can be controlled within the qualified range, thus achieving the objective of stabilizing alumina production and reducing production costs. The method provided by the present invention can accurately compensate the concentration value measured by the on-line instrument, and the compensated concentration value can follow the actual change trend; moreover, the measurement accuracy can meet the needs of actual production.

DETAILED DESCRIPTION OF THE INVENTION

Figure 1:
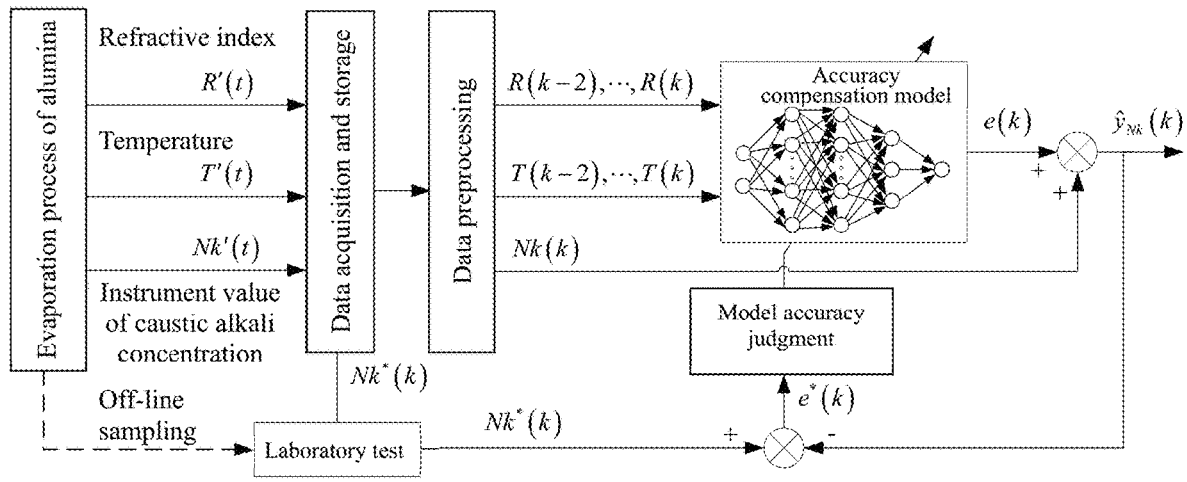
FIG. 1 is a structural diagram of an accuracy compensation algorithm for a caustic alkali concentration measuring device described in an embodiment of the present invention.
Figure 2:
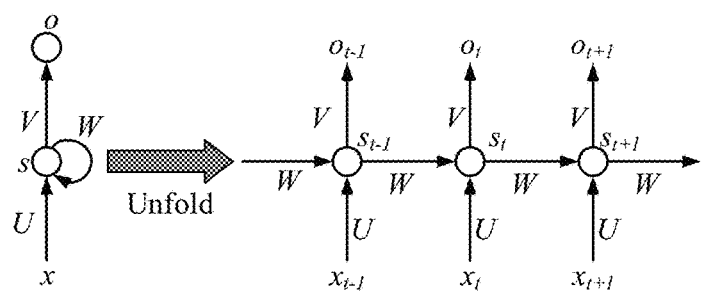
FIG. 2 is a structural diagram of a recurrent neural network described in an embodiment of the present invention.
Figure 3:
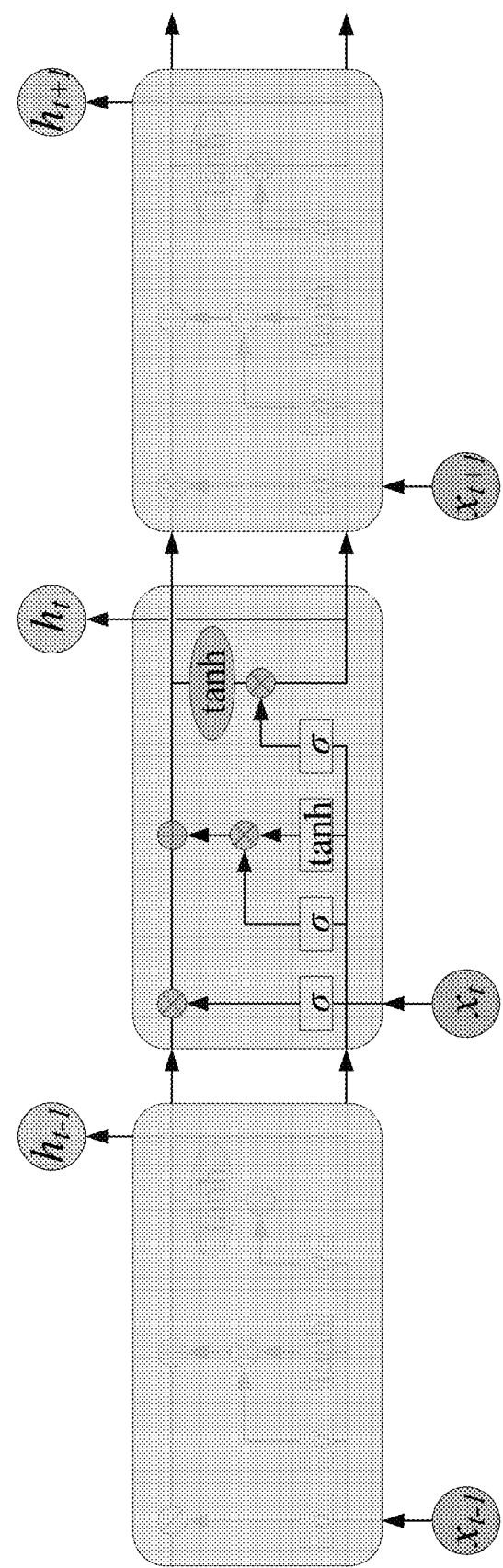
FIG. 3 is a structural diagram of a double-layer LSTM network described in an embodiment of the present invention.

In order to better explain the present invention and facilitate understanding, the present invention will be described in detail by some embodiments with reference to the drawings.

The embodiment of the present invention discloses an accuracy compensation method for a discharge caustic alkali concentration measuring device in an evaporation process, which comprises the following steps:

step 1. data acquisition: collecting process data of alkali liquor refractive index, temperature and instrument values and laboratory values of caustic alkali concentration in the evaporation process;

step 2. data preprocessing: performing sliding average filtering, time series matching and normalization to obtain preprocessed process data;

step 3. inputting the preprocessed process data into an accuracy compensation model of the caustic alkali concentration measuring device to obtain compensation values;

step 4. adding the compensation values of the caustic alkali concentration the instrument values and to realize the on-line compensation of the caustic alkali concentration.

In this embodiment, during the sliding average filtering in step 2, a window length of the sliding average filtering is set, that is, the number of points of the sliding average filtering is N, and the filtering formula is:

$$X(t) = \frac{1}{N}\sum_{i=0}^{N-1} X'(t-i) \quad (7)$$

wherein X(t) is the value at time t after filtering, X'(t) is the value of the original data at time t, and N is the window length of the sliding average filtering.

In this embodiment, during the time series matching process in step 2, the process data of 2 hours is divided into 3 parts according to an optimized control period of 40 minutes, and each part takes an average value of the process data of 40 minutes, the average value corresponding to a laboratory data of a previous sampling;

wherein a formula for the time series matching is:

$$\begin{cases} X(k) = \frac{1}{40}\sum_{i=0}^{39} X(i) \\ X(k+1) = \frac{1}{40}\sum_{i=40}^{79} X(i) \\ X(k+2) = \frac{1}{40}\sum_{i=80}^{119} X(i) \end{cases} \quad (8)$$

wherein, X(i) is a value at the $i^{th}$ time after filtering, and X(k) is process data matching a laboratory value at the $k^{th}$ point.

In this embodiment, the normalization process adopted in step 2 normalizes the input and output variable states used in the accuracy compensation model of the caustic alkali concentration measuring device:

$$\hat{x}_n = \frac{x_n - x_{min}}{x_{max} - x_{min}} \quad (9)$$

wherein, for a historical data $X=[x_1, \ldots, x_n]$ of a certain variable data, $x_n$ represents a state of the variable at the $n^{th}$ point, $x_{max}$ represents the maximum value of the variable in all the historical data, and $x_{min}$ represents the minimum value of the variable in all the historical data.

The input variables are preprocessed process data, and the output variables are the compensation values.

In this embodiment, the compensation method further comprises constructing an accuracy compensation model of the caustic alkali concentration measuring device, and training model parameters.

In this embodiment, constructing the accuracy compensation model of the caustic alkali concentration measuring device comprises the following steps:

Taking selected historical process data and the errors between historical instrument values of the caustic alkali concentration and historical laboratory values as input and output training data of the accuracy compensation model of the caustic alkali concentration measuring device, and using a deep learning algorithm to construct the accuracy compensation model;

Using a double-layer LSTM network for the deep learning algorithm to establish the accuracy compensation model of the caustic alkali concentration measuring device.

In this embodiment, the compensation method further comprises evaluating the accuracy compensation model of the caustic alkali concentration measuring device by using a root mean square error, a mean absolute error, and a mean absolute percentage error;

wherein a formula for calculating the root mean square error is:

$$RMSE = \sqrt{\frac{\sum_{i=0}^{N-1}(y_i - \hat{y}_i)^2}{N}} \quad (10)$$

wherein a formula for calculating the mean absolute error is:

$$RMSE = \sqrt{\frac{\sum_{i=1}^{N}(y_i - \hat{y}_i)^2}{N}} \quad (11)$$

wherein a formula for calculating the mean absolute percentage error is:

$$MAPE = \frac{100}{N}\sum_{i=1}^{N}\left|\frac{y_i - \hat{y}_i}{y_i}\right| \quad (12)$$

wherein, $y_i$ is laboratory values of the $i^{th}$ group of samples, and $\hat{y}_j$ is compensated caustic alkali concentration values of the $i^{th}$ group of samples.

As shown in FIG. 1, the accuracy compensation method for a discharge caustic alkali concentration measuring device in an evaporation process provided by the present invention comprises the following steps:

Step 1: Data Acquisition

Collecting process production parameter data and off-line sampling laboratory data; wherein the process data is obtained by reading the PHD (Process History Database) database of evaporation process with a time interval of 1 minute, including collecting the refractive index R(k) of discharging alkali liquor, the temperature T(k) of discharging alkali liquor and the instrument value of the caustic alkali concentration; the laboratory data $y_{Nk}(k)$ are obtained by accessing the enterprise MES system with a time interval of 2 hours. At the same time, the collected data are stored in the local disk in the form of increasing time tags, and the storage format is csv file.

Step 2: Data Preprocessing

Performing sliding average filtering on the three types of process data collected in Step 1. The process data is formed into a data matrix $X=[x_1,x_2,x_3]$. The window length of the sliding average filtering is set, that is, the average number of sliding average filtering points is 10, and the filtering formula of each column is:

$$X(t) = \frac{1}{10}\sum_{i=0}^{9} X'(t-i) \quad (13)$$

wherein, X(t) is a value at time t after filtering, X'(t) is a value of the original data at time t, and N is the window length of the sliding average filtering.

Time series matching: As the sampling periods of process data and laboratory data are different (sampling period: 1 minute for process data, 2 hours for laboratory data), in order to make full use of process data and extract its characteristics, the process data of 2 hours is divided into 3 parts according to an optimized control period of 40 minutes, and each part takes an average value of the process data of 40 minutes, the average value corresponds to a laboratory data of the previous sampling. The time series matching formula is:

$$\begin{cases} X(k) = \frac{1}{40}\sum_{i=0}^{39} X(i) \\ X(k+1) = \frac{1}{40}\sum_{i=40}^{79} X(i) \\ X(k+2) = \frac{1}{40}\sum_{i=80}^{119} X(i) \end{cases} \quad (14)$$

wherein, X(i) is a value at the $i^{th}$ time after filtering, and X(k) is process data matching a laboratory value at the $k^{th}$ point.

For the data from time series matching, the input and output variables of accuracy compensation model of the caustic alkali concentration measuring device in evaporation process are divided, with refractive index and temperature as input variables, and the error between instrument value and laboratory value of the caustic alkali concentration as output variables.

Normalization: All the input and output variable states used in the evaporation process accuracy compensation model are normalized;

$$\hat{x}_n = \frac{x_n - x_{min}}{x_{max} - x_{min}} \tag{15}$$

wherein, for the historical data $D=[x_1, \ldots, x_n]$ of a certain variable, $x_n$ represents the state of the variable at the $n^{th}$ time; $x_{max}$ represents the maximum value of the variable in all historical data; xmin represents the minimum value of the variable in all historical data.

Step 3: Constructing an Accuracy Compensation Model of the Caustic Alkali Concentration Measuring Device, and Training Model Parameters.

There are 10,500 groups of input and output data after data processing, of which 8,000 are used for training and 2,500 for testing. With the selected refractive index and temperature data as input data, and the error between concentration meter value and laboratory value as output data, a deep learning accuracy compensation model is constructed by using deep learning algorithm. A preferred recurrent neural network structure of the deep learning algorithm for processing time series data is shown in FIG. 5.

Figure 5:
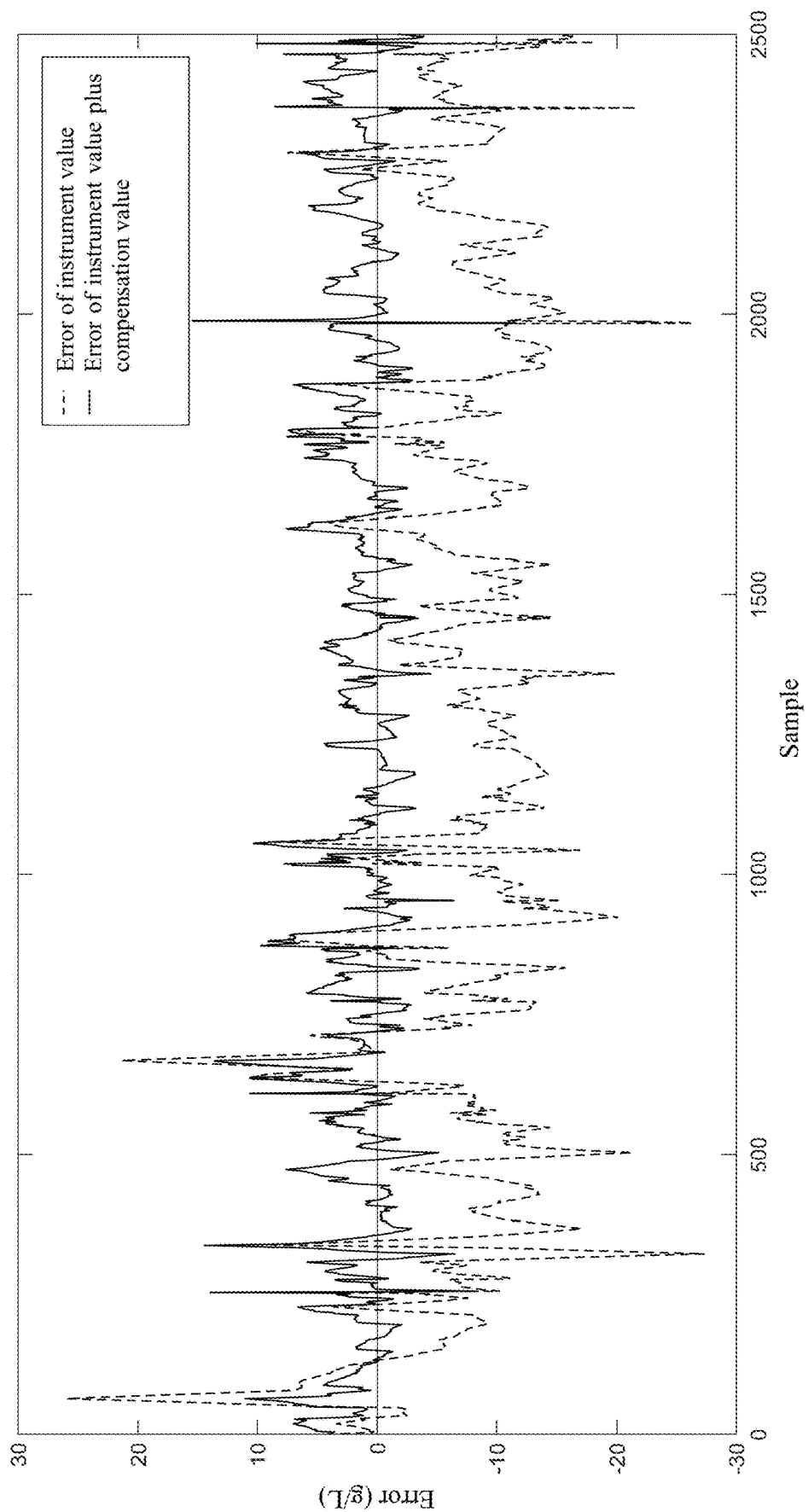
FIG. 5 is an error comparison diagram of concentration values and laboratory values before and after accuracy compensation of the caustic alkali concentration measuring device described in an embodiment of the present invention.

The left part in FIG. 5 is a recurrent structure of the recurrent neural network, which represents that the input of the current hidden layer includes the output of the hidden layer at the previous time. The network structure is expanded to get the right part in FIG. 5, wherein W, U and V are weights, $x_t$ is the input at time t, and $s_t$ is the hidden state at time t, that is, the hidden layer output, which is the memory unit of the network. $o_t$ is the output at time t. The mathematical formula of the recurrent neural network is as follows:

$$s_t = f(Ux_t + Ws_{t-1}) \tag{16}$$

$$o_t = \text{soft max}(Vs_t) \tag{17}$$

wherein, $f$ is usually a nonlinear activation function, such as tanh and relu. $s_t$ is obtained from the hidden output $s_{t-1}$ at the previous time and the input $x_t$ at the current time. The softmax function is the activation function of the output layer, and is often used in classification problems and mapping the output to a probability distribution of (0,1).

As the traditional RNN model has the problems of vanishing gradient and exploding gradient, especially when the series is very long, the traditional RNN model cannot be used directly at this time, but long short-term memory network (LSTM), which is a special case of RNN, is widely used.

Figure 6:
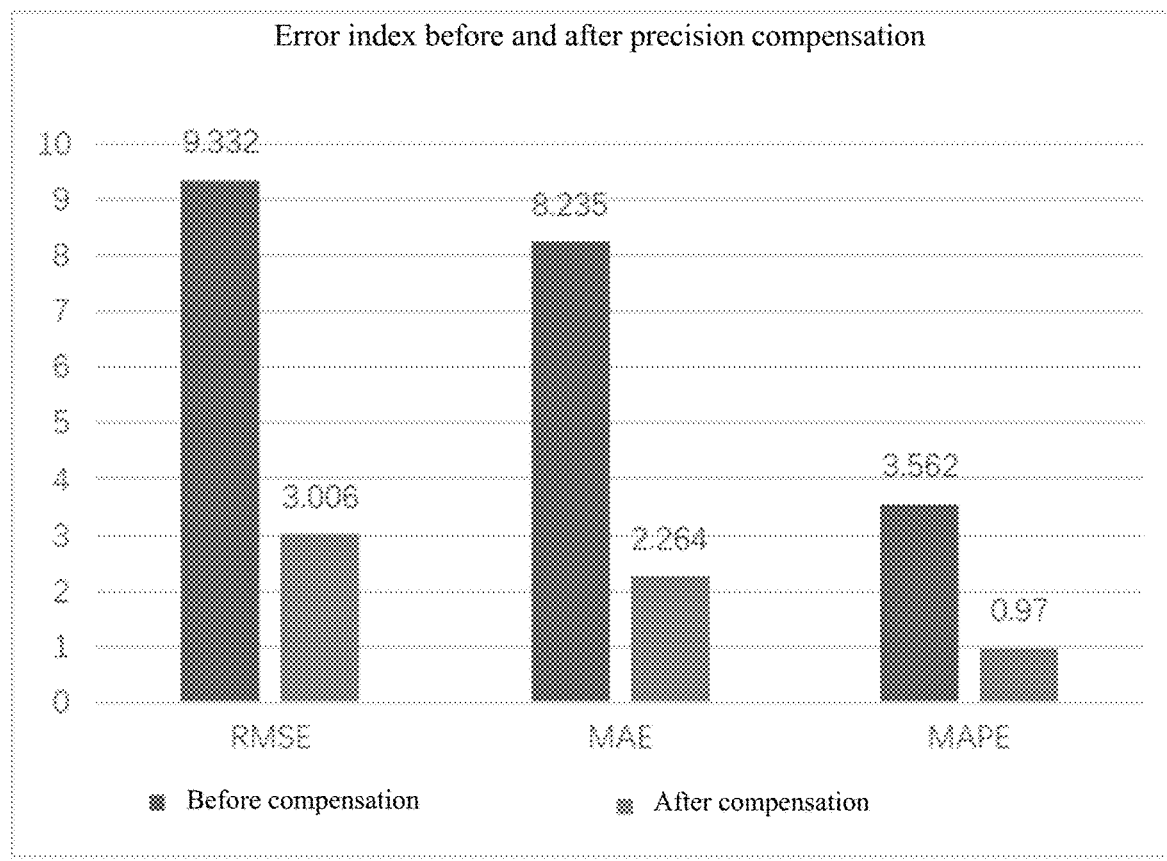
FIG. 6 is an error evaluation index diagram before and after accuracy compensation of the caustic alkali concentration measuring device described in an embodiment of the present invention.

Long short-term memory network (LSTM) is a special type of RNN. The main difference between LSTM and RNN is that LSTM adds a "processor" to the algorithm to judge whether the information is useful or not. The structure on which the processor acts is called "cell", as shown in FIG. 6. There are three gates in a cell, which are called input gate, forgetting gate and output gate. When a message enters the LSTM network, it can be judged whether it is useful according to the rules. Only the information that conforms to the algorithm authentication will be left, and the non-conforming information will be forgotten through the forgetting gate.

The operating principle of the cell structure can be expressed by formulas (18) to (22):

$$f_t = \sigma(W_f \cdot [h_{t-1}, x_t] + b_f) \tag{18}$$

$$i_t = \sigma(W_i \cdot [h_{t-1}, x_t] + b_i) \tag{19}$$

$$C_t = f_t * C_{t-1} + i_t * \tanh(W_C \cdot [h_{t-1}, x_t] + b_C) \tag{20}$$

$$o_t = \sigma(W_o \cdot [h_{t-1}, x_t] + b_o) \tag{21}$$

$$h_t = o_t * \tanh(C_t) \tag{22}$$

wherein, $h_t$ represents all the outputs of the LSTM unit at time t; $W_f$, $W_i$, $W_C$, and $W_o$ are the weight matrix composed of coefficients; $b_f$, $b_i$, $b_c$, and $b_o$ are the bias vectors of the corresponding weights; σ is the activation function sigmoid, and tanh is the activation function; · is the point multiplication operation; $C_t$ represents the calculation method of the memory cell at time t; $f_t$, $i_t$, and $o_t$ are the calculation methods of the input gate, forgetting gate and output gate at time t, respectively. It can be seen from FIG. 6 that the outputs of the input gate, the forgetting gate and the output gate are respectively connected to a multiplication element, thereby controlling the input and output of the information flow and the state of the cell unit, respectively.

The accuracy compensation model of the caustic alkali concentration measuring device is constructed by using double-layer LSTM networks and one fully connected layer. The accuracy compensation model is trained and tested by using the training set and test set divided previously. The root mean square error is used as the error function for error back propagation learning of neural network. The calculation formula of mean square error is:

$$MSE = \frac{\sum_{i=1}^{N}(y_i - \hat{y}_i)^2}{N} \tag{23}$$

Add the compensation value obtained by denormalizing the output of the accuracy compensation model of the caustic alkali concentration measuring device in Step 3 to the output value of the measuring device to obtain the predicted value of the caustic alkali concentration, as shown in the following formula:

$$\hat{y}_{Nk}(k) Nk(k) + e(k) \tag{24}$$

wherein, $\hat{y}_{Nk}(k)$ is the predicted value of the caustic alkali concentration by the accuracy compensation algorithm, Nk(k) represents the output value of the caustic alkali concentration measuring device, and e(k) represents the output value of the accuracy compensation model based on deep learning.

Figure 4:
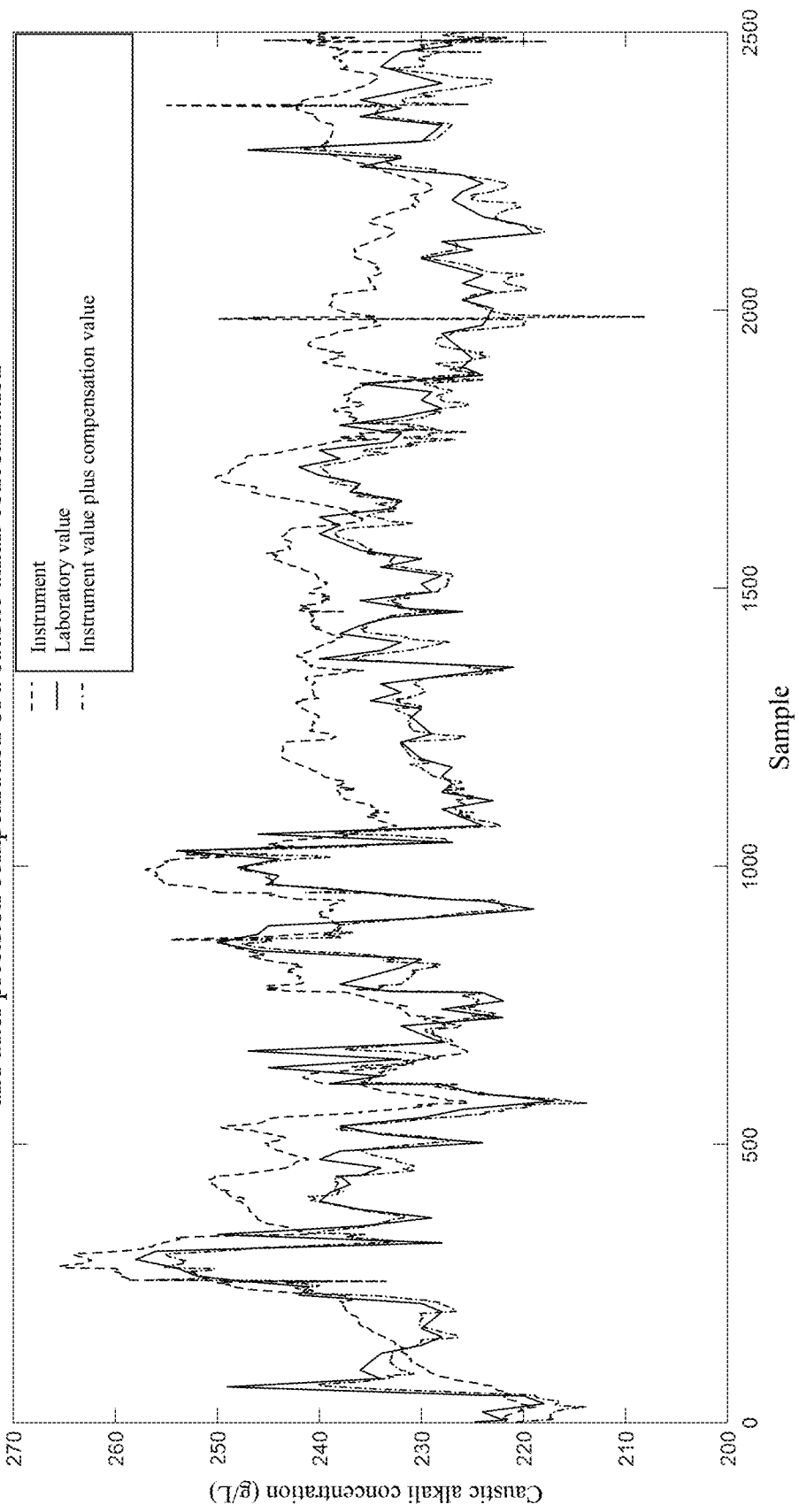
FIG. 4 is a comparison diagram of concentration values and laboratory values before and after accuracy compensation of a caustic alkali concentration measuring device described in an embodiment of the present invention.

Step 4: Prediction of Real-Time Compensation of the Caustic Alkali Concentration The prediction results are shown in FIGS. 4 and 5. It can be seen from FIG. 4 and FIG. 5 that the effect of the caustic alkali concentration value following the laboratory value after compensation is better than that before compensation, and the error between the caustic alkali concentration value and the laboratory value is obviously smaller.

The predicted value of the caustic alkali concentration by the accuracy compensation algorithm and the output value of the caustic alkali concentration measuring device are evaluated using root mean square error, mean absolute error, and mean absolute percentage error:

wherein a formula for calculating the root mean square error is:

$$RMSE = \sqrt{\frac{\sum_{i=1}^{N}(y_i - \hat{y}_i)^2}{N}} \quad (25)$$

wherein a formula for calculating the mean absolute error is:

$$MAE = \frac{\sum_{i=1}^{N}|y_i - \hat{y}_i|}{N} \quad (26)$$

wherein a formula for calculating the mean absolute percentage error is:

$$MAPE = \frac{100}{N}\sum_{i=1}^{N}\left|\frac{y_i - \hat{y}_i}{y_i}\right| \quad (27)$$

wherein, $y_i$ is the laboratory values of the $i^{th}$ group of samples, and $\hat{y}_i$ is the caustic alkali concentration values of the $i^{th}$ group of samples after compensation.

The index calculation results are shown in Table 1 and FIG. 6. The RMSE (root mean square error) index before compensation is 9.332, and the RMSE index after compensation is 3.006; the MAE (mean absolute error) index before compensation is 8.235, and the MAE index after compensation is 2.264; the MAPE (mean absolute percentage error) index before compensation is 3.562, and the MAPE index after compensation is 0.97; thus after compensation, the RMSE index is 67.8% higher than that before compensation, the MAE index is 72.5% higher than that before compensation, the MAPE index is 72.8% higher than that before compensation.

TABLE 1

Error evaluation index table of the caustic alkali concentration measuring device before and after compensation

|  | RMSE | MAE | MAPE |
| --- | --- | --- | --- |
| Before compensation | 9.332 | 8.235 | 3.562 |
| After compensation | 3.006 | 2.264 | 0.97 |

Figure 7:
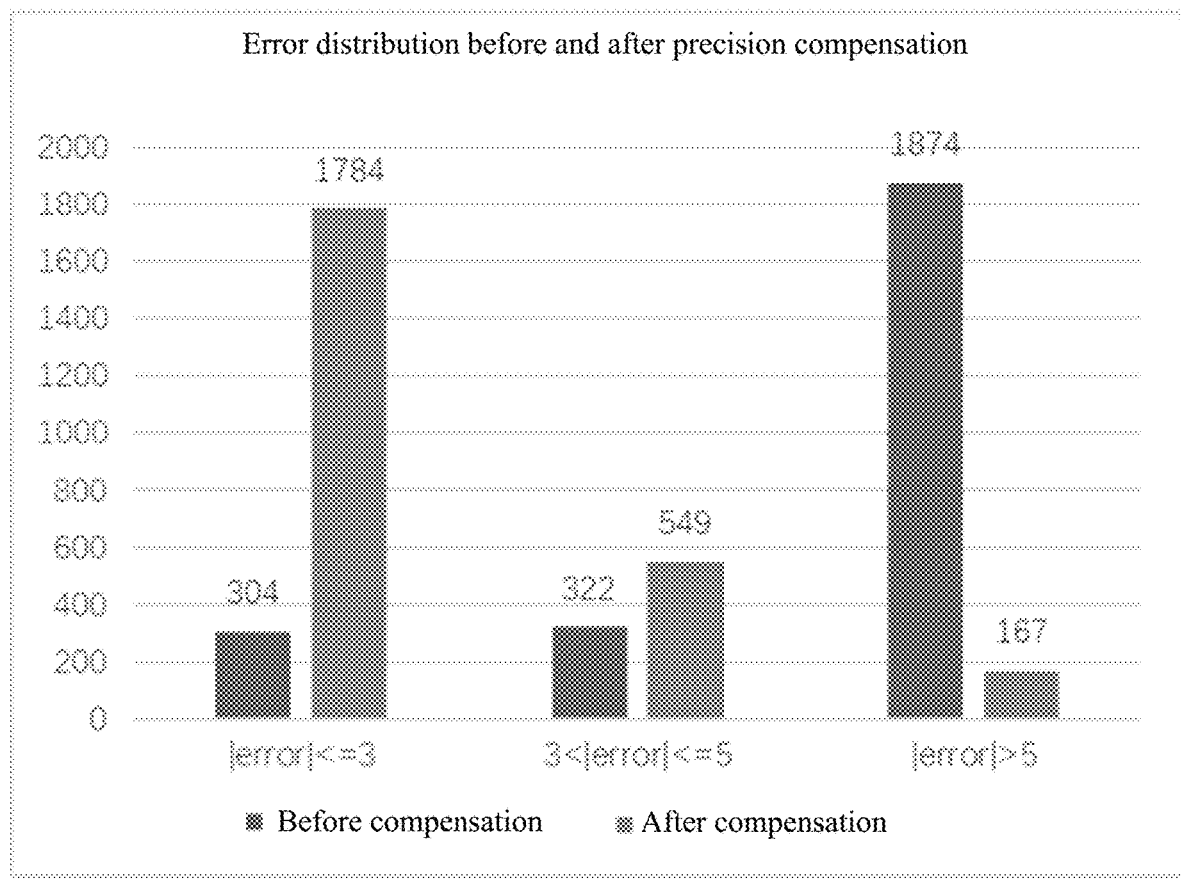
FIG. 7 is an error distribution diagram before and after accuracy compensation of the caustic alkali concentration measuring device described in an embodiment of the present invention.

The distribution of errors before and after compensation is shown in Table 2 and FIG. 7. In view of the fact that the caustic alkali concentration value obtained by the laboratory may have a certain error, therefore, the allowable error between the instrument value and the laboratory value is defined within 3 g/l, and the error within 3 g/l is considered as qualified when the caustic concentration value after compensation is compared with the laboratory value. It can be seen from the FIG. 7 that the errors before compensation are mostly above 5 g/l, and the errors after compensation are mostly below 3 g/l. The qualification rate of the caustic alkali concentration value before compensation is 12.16%. After introducing the accuracy compensation model of the caustic alkali concentration measuring device according to the present invention, the qualification rate of the caustic alkali concentration value after compensation is 71.36%, which is 59.2% higher than that before compensation, having obvious accuracy compensation effect.

TABLE 2

Error distribution table of the caustic alkali concentration measuring device before and after accuracy compensation

|  | |error| <= 3 | 3 < |error| <= 5 | |error| > 5 |
| --- | --- | --- | --- |
| Before compensation | 304 | 322 | 1874 |
| After compensation | 1784 | 549 | 167 |

In conclusion, the accuracy compensation model of the caustic alkali concentration measuring device has high accuracy, reliability, and accuracy.

In this embodiment, a model accuracy judgment module is also constructed. When the accuracy compensation model of the caustic alkali concentration measuring device cannot meet the requirements, it is necessary to retrain and correct the accuracy compensation model. Through the recent accumulated process data and laboratory values, the new model is trained to realize the long-term, stable, and accurate on-line compensation of the accuracy compensation model.

The technical principle of the present invention has been described above in combination with embodiments. These descriptions are only for explaining the principle of the present invention and cannot be interpreted as limiting the protection scope of the present invention in any way. Base on the description herein, those skilled in the art can think of other specific modes for carrying out the invention without creative work, and these modes will fall within the protection scope of the present invention.

The invention claimed is:

1. A method for compensating an accuracy of a discharge caustic alkali concentration measuring device, wherein the device is used monitoring an alkali liquor in an evaporation process, comprising the following steps:

step 1. measuring the alkali liquor during the evaporation process to obtain process data comprising a refractive index, a temperature, an instrument value of alkalinity measured real-time using an on-line instrument, and a laboratory value of alkalinity measured off-line in a laboratory;

step 2. performing sliding average filtering, time series matching and normalization on the process data collected in step 1 to obtain preprocessed process data;

step 3. constructing an accuracy compensation model and inputting the preprocessed process data into the accuracy compensation model of the caustic alkali concentration measuring device to obtain a compensation value; and step 4 adding the compensation value of the caustic alkali concentration to the instrument value to realize the on-line compensation of the caustic alkali concentration, wherein constructing the accuracy compensation model comprises training a double-layer Long Short-Term Memory (LSTM) network using historical refractive index data and historical temperature data as input training data and errors between historical instrument values and historical laboratory values as output training data.

2. The compensation method according to claim 1, wherein:

during the sliding average filtering process in step 2, a window length of the sliding average filtering is set, wherein a number of points of the sliding average filtering is N, and the filtering formula is:

$$X(t) = \frac{1}{N}\sum_{i=0}^{N-1} X'(t-i) \qquad (1)$$

wherein $X(t)$ is a value at time t after filtering, $X'(t)$ is a value of original data at time t, and N is the window length of the sliding average filtering.

3. The compensation method according to claim 1, wherein, during the time series matching process in step 2, the process data of a 2 hours duration is divided into 3 parts of 40 minutes in duration each, and an average value of the process data in each part corresponds to laboratory data of the previous sampling;
wherein a formula for the time series matching is:

$$\begin{cases} X(k) = \frac{1}{40}\sum_{i=0}^{39} X(i) \\ X(k+1) = \frac{1}{40}\sum_{i=40}^{79} X(i) \\ X(k+2) = \frac{1}{40}\sum_{i=80}^{119} X(i) \end{cases} \qquad (2)$$

wherein $X(i)$ is a value at the $i^{th}$ time after filtering, and $X(k)$ is process data matching a laboratory value at the $k^{th}$ point.

4. The compensation method according to claim 1, wherein the normalization in step 2 normalizes states of input and output variables used in the accuracy compensation model of the caustic alkali concentration measuring device according to:

$$\hat{x}_n = \frac{x_n - x_{min}}{x_{max} - x_{min}} \qquad (3)$$

wherein, for a historical data $X=[x_1, \ldots, x_n]$ of a certain variable data, $x_n$ represents a state of the variable at the $n^{th}$ point; $x_{max}$ represents the maximum value of the variable in all the historical data; and $x_{min}$ represents the minimum value of the variable in all the historical data, and
wherein the input variables are preprocessed process data and the output variables are the compensation values.

5. The compensation method according to claim 1, wherein:
the compensation method further comprises evaluating the accuracy compensation model of the caustic alkali concentration measuring device by using a root mean square error, a mean absolute error, and a mean absolute percentage error,
wherein a formula for calculating the root mean square error is:

$$RMSE = \sqrt{\frac{\sum_{i=1}^{N}(y_i - \hat{y}_i)^2}{N}}, \qquad (4)$$

wherein a formula for calculating the mean absolute error is:

$$MAE = \frac{\sum_{i=1}^{N}|y_i - \hat{y}_i|}{N}, \qquad (5)$$

wherein a formula for calculating the mean absolute percentage error is:

$$MAPE = \frac{100}{N}\sum_{i=1}^{N}\left|\frac{y_i - \hat{y}_i}{y_i}\right|, \qquad (6)$$

wherein $y_t$ is laboratory values of the $i^{th}$ group of samples and $\hat{y}_i$ is compensated caustic alkali concentration values of the $i^{th}$ group of samples.

* * * * *